United States Patent [19]
Boettner et al.

[11] Patent Number: 5,811,130
[45] Date of Patent: Sep. 22, 1998

[54] INJECTABLE QUINOLONE FORMULATIONS

[75] Inventors: Wayne A. Boettner, Noank, Conn.; Peter C. Canning, Fort Collins, Colo.

[73] Assignee: Pfizer Inc., New York, N.Y.

[21] Appl. No.: 769,809

[22] Filed: Dec. 19, 1996

Related U.S. Application Data

[60] Provisional application No. 60/009,052 Dec. 21, 1993.

[51] Int. Cl.⁶ .......................... A61K 33/32; A61K 33/08; A61K 31/495; A61K 31/50
[52] U.S. Cl. .......................... 424/643; 424/692; 514/254
[58] Field of Search ................. 424/643, 692; 514/254

[56] References Cited

U.S. PATENT DOCUMENTS

| | | | |
|---|---|---|---|
| 4,772,605 | 9/1988 | Naik et al. | 514/254 |
| 5,082,863 | 1/1992 | Apelian et al. | 514/618 |
| 5,084,276 | 1/1992 | Yunker et al. | 424/422 |
| 5,223,246 | 6/1993 | Kondo et al. | 424/44 |
| 5,334,589 | 8/1994 | Al-Razzak et al. | 514/185 |

FOREIGN PATENT DOCUMENTS 63-188626   8/1988   Japan.

*Primary Examiner*—Kimberly Jordan
*Attorney, Agent, or Firm*—Peter C. Richardson; Paul H. Ginsburg; Gezina Holtrust

[57] ABSTRACT

Aqueous pharmaceutical solutions suitable for injection into a host, having improved injection site toleration, comprise danofloxacin or its pharmaceutically acceptable salts and a magnesium or zinc compound. The zinc compound in addition requires the presence of a co-solvent.

12 Claims, No Drawings

INJECTABLE QUINOLONE FORMULATIONS

This application claims of Provisional Appln No. 60/009,052, filed Dec. 21, 1993.

This invention relates to aqueous pharmaceutical solutions which are suitable for injection into animals and comprise the antibacterial agent danofloxacin with a magnesium or zinc compound.

It is generally known that quinolone carboxylic acids on injection into a host have a tendency to cause tissue damage at the injection site. One way of alleviating this problem is disclosed in U.S. Pat. No. 5,235,054 describing introduction of a 3-carboxyaldehyde prodrug group to replace the 3-carboxy group in certain quinolone carboxylic acids.

U.S. Pat. Nos. 4,018,889 and 4,126,680 disclose injectable, high dosage, aqueous solutions of tetracycline antibiotics in the co-solvents 2-pyrrolidone, and caprolactam or 2-piperidone, respectively. The patents also mention addition of magnesium ions to the aqueous solutions to increase the physical stability, minimizing precipitation of the solutions by formation of magnesium-tetracycline chelates.

The present invention improves injection site toleration of injectable aqueous danofloxacin solutions by incorporation of certain metal compounds. It is believed that the metal compounds form complexes with danofloxacin so increasing the solubility thereof in water. It is further believed that the increased water solubility results in the improved toleration at the injection site.

SUMMARY OF THE INVENTION

This invention relates to an aqueous pharmaceutical solution which is suitable thereof in an amount sufficient for the treatment of bacterial infections, and (1) a magnesium compound, or (2) a mixture of a zinc compound with a co-solvent; said compounds and said co-solvent being present in amounts which are sufficient for improved toleration at the injection site.

In a preferred embodiment of the invention, said magnesium compound is present together with a co-solvent. In a further preferred embodiment said co-solvent of the magnesium compound or the zinc compound is at least one of 2-pyrrolidone, propylene glycol, polyethylene glycol, and N-methyl pyrrolidone, each optionally together with polyvinylpyrrolidone.

The aqueous pharmaceutical solution preferably contains an antioxidant, such as sodium formaldehyde sulfoxylate for increased stability. The solution is usually adjusted to a pH of about 5 to about 9.5, preferably from about 6.5 to about 9.0.

The invention also comprises a method for the treatment of bacterial infections in a host by injecting into said host an aqueous pharmaceutical solution comprising danofloxacin or a pharmaceutically acceptable salt thereof in an amount sufficient for the treatment of bacterial infections, and a (1) magnesium compound, or a (2) zinc compound in admixture with a co-solvent; said compounds and said co-solvent being present in amounts which are sufficient for improved toleration at the injection site.

DETAILED DESCRIPTION OF THE INVENTION

Danofloxacin is 1-cyclopropyl-6-fluoro-7-{(1S,4S)-5-methyl-2,5-diazabicyclo[2.2.1]hept-2-yl}-4-oxo-3-quinoline carboxylic acid, disclosed in U.S. Pat. No. 4,861,779.

Suitable magnesium compounds of use in the invention include magnesium oxide and magnesium chloride. The magnesium compound is present in amounts that are sufficient to increase injection site toleration. The molar ratio of magnesium to danofloxacin or a pharmaceutically acceptable salt thereof (hereafter "the active compound") usually ranges from about 0.25 to about 2, preferably about 0.8 to 1.2, such as about 1.

The zinc compound of use in the invention includes zinc oxide and zinc acetate. The molar ratio of zinc to the active compound ranges from about 0.3 to about 0.7, preferably about 0.5.

A co-solvent is understood to be a pharmaceutically acceptable liquid that can be added to an injectable formulation. It has been found that the zinc compound must be administered with a co-solvent to be effective in improving the injection site toleration. The amount of co-solvent together with the amount of zinc compound is such that improved injection site toleration is obtained. Small amounts of a few, e.g., 1 to 3, weight percent of co-solvent based on the zinc compound may improve injection site toleration. However, usually higher amounts of about 30 to 50% by weight of co-solvent will be used to obtain optimum injection site toleration.

It was found that a co-solvent when used in combination with a magnesium compound increased the physical stability of the injectable solution containing the magnesium compound. The amounts of co-solvent to be used are from 0 to 50% by weight, usually from about 15 to 45% by weight, based on the magnesium compound.

Examples of co-solvents are at least one of 2-pyrrididone, propylene glycol, polyethylene glycol and N-methylpyrrolidone. The polyethylene glycol may have a molecular weight of from about 200 to about 400, preferably about 300.

Polyvinylpyrrolidone (PVP) having a molecular weight of between about 5,000 and 100,000 (K-12 to K-30) may be present in a concentration of from about 1 to 10%, e.g., about 5%, by weight to increase tissue toleration.

The stability of the present aqueous compositions is enhanced by the use of antioxidants at levels of from about 0.01 to about 1.0% by weight. Examples of suitable antioxidants are at least one of sodium metabisulfite, sodium sulfite, sodium formaldehyde sulfoxylate, sodium formaldehyde sulfoxylate with ethylenediamine tetraacetic acid (EDTA), sodium thiosulfate, acetylcysteine, thioglycerol, butylated hydroxy anisole (BHA), butylated hydroxy toluene (BHT), $\alpha$-tocopherol, monoethanolamine, triethanolamine, citric acid, tartaric acid, EDTA,EDTA with citric acid, EDTA with BHA, EDTA with sodium metabisulfite, and triethanolamine with BHA.

The pH of the aqueous compositions of the invention generally ranges from about 5 to about 9.5, suitably from 6.5 to 9.0, most preferably 7.5, to obtain physically stable solutions. Suitable components to adjust the pH include bases and acids, such as sodium hydroxide or monoethanolamine, and hydrogen chloride or lactic acid, respectively.

The pharmaceutically acceptable acid addition salts of danofloxacin include salts with pharmaceutically acceptable acids such as acetic, lactic, succininic, maleic, tartaric, citric, gluconic, ascorbic, benzoic, methanesulfonic, cinnamic, furmaric, phosphoric, hydrochloric, hydrobromic, hydroiodic, sulfam, pivalic, stearic and sulfonic acid. These salts are prepared in a conventional manner by treating a solution or suspension of the quinolone compound with about one chemical equivalent of a pharmaceutically acceptable acid.

The solutions of the invention are readily prepared by mixing the co-solvent, when present, with the PVP, when present, and water, until the PVP is dissolved. The solution is conveniently heated, e.g., to 50° C., and the magnesium or zinc compound added. After addition of the active compound and continued stirring, a solution is usually formed. The composition may be held at a slightly elevated temperature during stirring. If necessary, either before or after addition of the active compound, the pH is adjusted by addition of a base or acid, and the remainder of the water is added to form a solution. In general, the solutions are prepared such that exposure to oxygen is reduced to minimize chemical degradation of the ingredients in the solutions.

It has been found that bioavailability and antibacterial activity in vivo of the present pharmaceutical compositions are comparable to those of the prior art.

The pharmaceutical solutions of the invention are conveniently injected into the host such as cattle by subcutaneous injection.

The dosage of the active compound may vary according to administration methods, age and weight of the host, severity of the infection and the like, and usually ranges from about 1 to 10 mg/kg/day. The aqueous solutions of the invention contain the active compound in an amount ranging from about 25 to 300 mg/mL, preferably from about 60 to about 200, such as 180 mg/mL.

The following standard procedure was used to evaluate the injection site toleration of the pharmaceutical solutions of the invention. Calves weighing 200–300 kg were injected subcutaneously with a pharmaceutical solution according to the invention either on a milligram per kilogram or on a volume dependent basis. Each formulation was administered at a minimum of three sites. Subcutaneous injections were made in the neck region. The calves were observed immediately post-injection for signs of intolerance (ie., pain). Injection sites were observed grossly and palpated to detect swelling at 24 hours post-injection and once weekly for the duration of the 28 day study. At 28 days post-injection, the calves were euthanized. The injection sites were removed and chilled overnight to facilitate examination. Subcutaneous sites were removed with the hide and underlying muscle intact. The injection sites were examined for gross lesions and the character and extent of the gross lesions were evaluated according to standard guidelines.

The subcutaneous injection sites were rated acceptable if there was no necrosis or a small amount of necrosis which could easily be trimmed from the site. They were rated unacceptable if there was marked fascia and/or muscle necrosis.

The following Examples illustrate the invention and do not limit the scope of the invention to the specific details therein. In general, during manufacture of the formulations in the Examples, exposure of the formulations to oxygen was reduced, e.g. by bubbling nitrogen through them and/or by maintaining a nitrogen head space in the vessel used. The formulations were packaged in vials whose head space was flushed with nitrogen.

EXAMPLE 1

The following formulation was prepared:

|  | g/500 ml |
| --- | --- |
| danofloxacin | 6.00 |
| 2-pyrrolidone | 40.02 |
| polyvinylpyrrolidone (PVP) | 5.01 |
| MgO | 0.68 |
| sodium formaldehyde sulfoxylate (SFS) | 0.20 |
| HCl | qs to pH 7.8 |
| water | qs to 100 mL |

The 2-pyrrolidone, the PVP, and the water estimated necessary to produce 200 mL of the formulation were combined and agitated until the PVP dissolved. The solution was heated to about 50° C. The sodium formaldehyde sulfoxylate was added and dissolved. The magnesium oxide was added. The resulting slurry was subdivided into two portions. The danofloxacin was added to a portion of the slurry weighing 94.04 g. The formulation was held at about 50° C. and agitated for approximately one hour. It had a cloudy gold appearance and contained some suspended matter. The formulation was cooled to room temperature and the pH adjusted to 7.8 with the HCl to form a solution. Following agitation for 2 hours, the pH of the solution was 8.0.

The solution contained 60 mg/mL of danofloxacin based on a potency of 1000 mg/g for the lot of danofloxacin used.

EXAMPLE 2

|  | g/500 mL |
| --- | --- |
| danofloxacin mesylate | 40.1 |
| 2-pyrrolidone | 198.2 |
| polyvinylpyrrolidone (PVP) | 24.8 |
| MgO | 3.3 |
| sodium formaldehyde sulfoxylate (SFS) | 1.0 |
| HCl | 1.6 |
| water | qs to 500 mL |

The 2-pyrrolidone, the PVP, and most of the water estimated necessary to produce 2000 mL of the formulation were combined and agitated until the PVP dissolved. The solution was heated to about 50° C. The sodium formaldehyde sulfoxylate was added and dissolved and then the magnesium oxide was added. The resulting slurry was cooled to room temperature and held for future use. The slurry was resuspended and 500 g was subdivided. The 500 g portion was heated to about 50° C., and the danofloxacin mesylate was added. After the formulation was held at about 50° C. and agitated for approximately one hour, it was yellow and contained a small amount of suspended material. After cooling to room temperature, the pH was adjusted to 8.3 with the HCl, and the formulation was agitated for approximately 22 hours. Following agitation, this formulation was a solution. A sufficient quantity of water was added to produce the desired volume of 500 mL. The pH of the resulting formulation was 8.3 and contained 60 mg/mL of danofloxacin based on a potency of 748 mg/g for the lot of danofloxacin mesylate used.

EXAMPLE 3

|  | g/600 mL |
| --- | --- |
| danofloxacin mesylate | 48.5 |
| 2-pyrrolidone | 240.0 |
| polyvinylpyrrolidone (PVP) | 30.1 |
| MgO | 4.0 |
| HCl | 2.1 |
| water | qs to 600 mL |

The 2-pyrrolidone, the PVP, and most of the water were combined and agitated until the PVP dissolved. The solution was heated to about 50° C., and the magnesium oxide was added. The danofloxacin mesylate was added to the resulting slurry. The formulation was held at about 50° C. and agitated for approximately one hour forming a gold hazy suspension with numerous fine particles. The suspension was cooled to room temperature and held overnight. After the pH was adjusted to 8.2 with the HCl, the formulation was agitated for approximately 20 hours to form a solution. A sufficient quantity of water was added to produce the desired volume of 600 mL. The pH of the formulation was 8.4.

The solution contained 60 mg/mL of danofloxacin based on a potency of 742 mg/g for the lot of danofloxacin mesylate used.

EXAMPLE 4

|  | g/50 mL |
| --- | --- |
| danofloxacin mesylate | 16.11 |
| 2-pyrrolidone | 16.99 |
| polyvinylpyrrolidone (PVP) | 2.51 |
| MgO | 1.35 |
| sodium formaldehyde sulfoxylate (SFS) | 0.10 |
| HCl | 1.49 |
| water | qs to 50 mL |

The 2-pyrrolidone, the PVP, and most of the water necessary to produce 100 mL of the formulation were combined and agitated until the PVP dissolved. The solution was heated to about 50° C. The magnesium oxide was added, then the sodium formaldehyde sulfoxylate and the danofloxacin mesylate. The resulting slurry was held at about 50° C. and agitated for approximately one hour resulting in a light brown formulation containing considerable suspended material. The formulation was subdivided and one half was cooled to room temperature. The pH was adjusted to 8.2 with the HCl and the formulation agitated overnight to form a clear, yellow solution. The volume of the solution was approximately 50 mL and the pH was 8.2.

The solution contained 240 mg/mL of danofloxacin based on a potency of 745 mg/g for the lot of danofloxacin mesylate used.

EXAMPLE 5

|  | g/50 mL |
| --- | --- |
| danofloxacin mesylate | 20.14 |
| 2-pyrrolidone | 14.53 |
| polyvinylpyrrolidone (PVP) | 2.51 |
| MgO | 1.68 |
| sodium formaldehyde sulfoxylate (SFS) | 0.10 |
| HCl | 0.76 |
| water | qs to 50 mL |

The 2-pyrrolidone, the PVP, and most of the water necessary to produce 100 mL of the formulation were combined and agitated until the PVP dissolved. The solution was heated to about 50° C. The magnesium oxide was added, then the sodium formaldehyde sulfoxylate and the danofloxacin mesylate. The resulting slurry was held at about 50° C. and agitated for approximately one hour to form a light brown formulation containing considerable suspended material. The formulation was subdivided: one half was cooled to room temperature, and the pH was adjusted to 8.3 with the HCl. The solution was agitated overnight to form a yellow, opalescent suspension. A sufficient quantity of water was added to produce the desired volume of 50 mL. The pH of the formulation was 8.3.

The formulation was centrifuged and the supernatant filtered through a 0.22 micron filter. The filtrate solution contained 298 mg/mL of danofloxacin.

EXAMPLE 6

|  | g/1000 mL |
| --- | --- |
| danofloxacin mesylate | 242.0 |
| 2-pyrrolidone | 400.0 |
| polyvinylpyrrolidone (PVP) | 50.1 |
| MgO | 20.2 |
| HCl | 18.0 |
| water | qs to 1000 mL |

The 2-pyrrolidone, the PVP, and a portion of the water were combined and agitated until the PVP dissolved. The solution was heated to about 50° C. The magnesium oxide was added. The danofloxacin mesylate was added to the resulting slurry. The formulation was held at about 50° C. and agitated for approximately one hour to form a dark brown formulation containing a small amount of suspended material. The formulation was cooled to room temperature and the pH was adjusted to 8.2 with the HCl. Following overnight agitation, a dark brown solution was formed. A sufficient quantity of water was added to produce the desired volume of 1000 mL. The pH of the solution was 8.4 and the solution contained 180 mg/mL of danofloxacin based on a potency of 745 mg/g for the lot of danofloxacin mesylate used.

EXAMPLE 7

|  | g/300 mL |
| --- | --- |
| danofloxacin mesylate | 72.4 |
| 2-pyrrolidone | 120.0 |
| polyvinylpyrrolidone (PVP) | 15.0 |
| MgO | 6.1 |
| sodium formaldehyde sulfoxylate (SFS) | 0.6 |
| HCl | 2.4 |
| water | qs to 300 mL |

The 2-pyrrolidone, the PVP, and a portion of the water were combined and agitated until the PVP dissolved. The solution was heated to about 50° C. The magnesium oxide was added. After the danofloxacin mesylate was added to the resulting slurry, the formulation was held at about 50° C. and agitated for approximately one hour. The sodium formaldehyde sulfoxylate was added, and the solution held at about 50° C. and agitated for less than 20 minutes. After the formulation was cooled to room temperature, the pH was adjusted to 8.1 with the HCl. After agitation overnight, the formulation was gold and contained a small amount of suspended material. A sufficient quantity of water was added to produce the desired volume of 300 mL and a pH of 8.4. The formulation was passed through a paper filter to remove a small amount of suspended material.

The solution formed contained 180 mg/mL of danofloxacin based on a potency of 745 mg/g for the lot of danofloxacin mesylate used.

EXAMPLE 8

|  | g/300 mL |
|---|---|
| danofloxacin mesylate | 72.5 |
| polyvinylpyrrolidone (PVP) | 15.0 |
| MgO | 3.0 |
| NaOH | 1.6 |
| water | qs to 300 mL |

The PVP and a portion of the water were combined and agitated until the PVP dissolved. The formed solution was heated to about 50° C. The magnesium oxide was added, and the danofloxacin mesylate was added to the resulting slurry. The formulation was held at about 50° C. and agitated for approximately one hour to form a dark brown solution. After the formulation was cooled to room temperature, the pH was adjusted to 8.0 with the NaOH. Following agitation overnight, the formulation was a dark brown solution. A sufficient quantity of water was added to produce the desired volume of 300 mL at a pH of 8.0.

The solution contained 180 mg/mL of danofloxacin based on a potency of 745 mg/g for the lot of danofloxacin mesylate used.

EXAMPLE 9

|  | g/300 mL |
|---|---|
| danofloxacin mesylate | 72.8 |
| polyvinylpyrrolidone (PVP) | 15.0 |
| MgO | 6.0 |
| lactic acid | 6.8 |
| water | qs to 300 mL |

The PVP and a portion of the water were combined and agitated until the PVP dissolved. The magnesium oxide was added, and the danofloxacin mesylate was added to the resulting slurry. After the formulation was agitated for a period of time, the pH was adjusted to 8.1 with the lactic acid. A sufficient quantity of water was added to produce the desired volume of 300 mL. Following agitation overnight, the formulation was a clear, light brown solution and the pH was 8.1.

The solution contained 180 mg/mL of danofloxacin based on a potency of 742 mg/g for the lot of danofloxacin mesylate used.

EXAMPLE 10

|  | g/300 mL |
|---|---|
| danofloxacin mesylate | 71.9 |
| 2-pyrrolidone | 118.5 |
| polyvinylpyrrolidone (PVP) | 14.9 |
| ZnO | 6.0 |
| NaOH | 3.7 |
| water | qs to 300 mL |

The 2-pyrrolidone, the PVP, and a portion of the water necessary to produce 400 mL of the formulation were combined and agitated until the PVP dissolved. The solution was heated to about 50° C. The zinc oxide was added, and the danofloxacin mesylate was added to the resulting slurry. The formulation was held at about 50° C., agitated for approximately one hour, subdivided, and cooled to room temperature. The pH was adjusted to 8.0 with the NaOH. A sufficient quantity of water was added to produce the desired volume of 300 mL at a pH of 8.0. The formulation was passed through a paper filter to remove a small amount of suspended material so resulting in a clear brown solution.

The solution contained 178 mg/mL of danofloxacin based on a potency of 742 mg/g for the lot of danofloxacin mesylate used.

EXAMPLE 11

|  | g/300 mL |
|---|---|
| danofloxacin mesylate | 72.8 |
| 2-pyrrolidone | 120.1 |
| zinc acetate | 13.7 |
| NaOH | 7.3 |
| water | qs to 300 mL |

The 2-pyrrolidone and a portion of the water were combined and the solution was heated to about 50° C. After addition of the zinc acetate and the danofloxacin, the formulation was heated to about 50° C., and held at that temperature and agitated for approximately one hour. The resulting formulation, which was dark brown with a small amount of suspended material, was cooled to room temperature with increased formation of suspended material. The pH was adjusted to 7.7 with the NaOH. A sufficient quantity of water was added to produce the desired volume of 300 mL. Following agitation overnight, the formulation was a solution with a pH of 7.7.

The solution contained 180 mg/mL of danofloxacin based on a potency of 742 mg/g for the lot of danofloxacin mesylate used.

EXAMPLE 12

|  | g/564 mL |
|---|---|
| danofloxacin mesylate | 133.8 |
| 2-pyrrolidone | 225.7 |
| polyvinylpyrrolidone (PVP) | 28.3 |
| MgO | 11.4 |
| sodium formaldehyde sulfoxylate (SFS) | 1.1 |
| HCl | 27.5 |
| water | qs to 564 mL |

The 2-pyrrolidone, the PVP, and a portion of the water necessary to produce 1000 mL of the formulation were combined and agitated until the PVP dissolved. After the solution was heated to about 50° C., the magnesium oxide was added. After the danofloxacin mesylate was added to the resulting slurry, the formulation was held at about 50° C. and agitated for approximately one hour to form a suspension. After cooling to room temperature, the pH of the formulation was adjusted to 5.9 with the HCl. Following agitation for approximately one hour, the formulation was a clear brown solution. A sufficient quantity of water was added to produce a volume of 1000 mL at a pH of 5.8. Approximately 563 mL of the formulation was heated to about 50° C., and the sodium formaldehyde sulfoxylate was added and dissolved with agitation. The formulation was held at about 50° C., agitated for approximately one hour and cooled to room temperature. The formulation was a clear yellow solution with a pH of 5.8.

The solution contained 180 mg/mL of danofloxacin based on a potency of 759 mg/g for the lot of danofloxacin mesylate used.

EXAMPLE 13

|  | g/694 mL |
| --- | --- |
| danofloxacin mesylate | 164.3 |
| 2-pyrrolidone | 277.1 |
| polyvinylpyrrolidone (PVP) | 34.7 |
| MgO | 14.0 |
| sodium formaldehyde sulfoxylate (SFS) | 1.4 |
| HCl | 0.7 |
| NaOH | 0.3 |
| water | qs to 694 mL |

The 2-pyrrolidone, the PVP, and a portion of the water necessary to produce 1000 mL of the formulation were combined and agitated until the PVP dissolved. The solution was heated to about 50° C., the magnesium oxide was added, and the danofloxacin mesylate was added to the resulting slurry. The formulation was held at about 50° C., agitated for approximately one hour to form a suspension and cooled to room temperature. The pH was 8.5. Following agitation overnight, the pH was 8.8 and a few suspended particles remained. A sufficient quantity of water was added to produce a volume of 1000 mL and a pH of 8.2. Approximately 693 mL of the formulation was heated to about 50° C., the sodium formaldehyde sulfoxylate was added, and dissolved with agitation. The formulation was held at about 50° C. for approximately one hour and cooled to room temperature resulting in a clear yellow solution with a pH of 8.8.

The solution contained 180 mg/mL of danofloxacin based on a potency of 759 mg/g for the lot of danofloxacin mesylate used.

EXAMPLE 14

|  | g/704 mL |
| --- | --- |
| danofloxacin mesylate | 166.9 |
| 2-pyrrolidone | 176.2 |
| polyvinylpyrrolidone (PVP) | 52.9 |
| MgO | 14.2 |
| sodium formaldehyde sulfoxylate (SFS) | 1.4 |
| HCl | 17.0 |
| water | qs to 704 mL |

The 2-pyrrolidone, the PVP, and a portion of the water necessary to produce 1000 mL of the formulation were combined and agitated until the PVP dissolved. The solution was heated to about 50° C., and the magnesium oxide was added. The danofloxacin mesylate was added to the resulting slurry. The formulation was held at about 50° C. and agitated for approximately one hour forming a suspension. After cooling to room temperature, the pH of the formulation was adjusted to 8.0 with a portion of the HCl. Following agitation overnight, the pH was 8.5, which was adjusted to 8.0 with additional HCl. The formulation was agitated for approximately two hours to form a clear brown solution. A sufficient quantity of water was added to produce a volume of 1000 mL and a pH of 8.2. Approximately 703 mL of the formulation was heated to about 50° C., the sodium form-aldehyde sulfoxylate was added and dissolved with agitation. The formulation was held at about 50° C., agitated for approximately one hour and cooled to room temperature forming a clear yellow solution which contained 180 mg/mL of danofloxacin based on a potency of 759 mg/g for the lot of danofloxacin mesylate used.

EXAMPLE 15

|  | g/1000 mL |
| --- | --- |
| danofloxacin mesylate | 237.6 |
| 2-pyrrolidone | 400.0 |
| polyvinylpyrrolidone (PVP) | 50.1 |
| zinc acetate | 40.8 |
| sodium formaldehyde sulfoxylate (SFS) | 2.0 |
| NaOH | 28.3 |
| water | qs to 1000 mL |

The 2-pyrrolidone, the PVP, and a portion of the water were combined and agitated until the PVP dissolved. The SFS was added to the solution and dissolved with agitation. The solution was heated to about 50° C. A portion of the zinc acetate and the danofloxacin mesylate were added. The formulation was held at about 50° C., agitated for approximately one hour and cooled to room temperature. The sodium hydroxide was added to the suspension in several portions. After the final addition, the pH was 8.0. The balance of the zinc was added and the formulation was heated to about 50° C., held at that temperature, agitated for approximately one hour and then cooled to room temperature. A sufficient quantity of water was added to produce 1000 mL of a clear yellow solution with a pH of 8.0. The solution contained 180 mg/mL of danofloxacin based on a potency of 759 mg/g for the lot of danofloxacin mesylate used.

EXAMPLE 16

|  | g/250 mL |
| --- | --- |
| danofloxacin mesylate | 59.3 |
| 2-pyrrolidone | 100.2 |
| polyvinylpyrrolidone (PVP) | 12.5 |
| magnesium chloride | 11.9 |
| sodium formaldehyde sulfoxylate (SFS) | 0.5 |
| NaOH | 6.5 |
| water | qs to 250 mL |

The 2-pyrrolidone, the PVP, and a portion of the water were combined and agitated until the PVP dissolved. The SFS was added to the solution and dissolved with agitation. The magnesium chloride and the danofloxacin mesylate were added. The pH was adjusted to 8.1 with the NaOH. Following agitation overnight, a sufficient quantity of water was added to produce 250 mL of a dark yellow solution with a pH of 7.8.

The solution contained 180 mg/mL of danofloxacin based on a potency of 759 mg/g for the lot of danofloxacin mesylate used.

EXAMPLE 17

|  | g/1000 mL |
| --- | --- |
| danofloxacin mesylate | 237.3 |
| propylene glycol | 250.0 |
| polyvinylpyrrolidone (PVP) | 50.1 |
| MgO | 20.1 |
| sodium formaldehyde sulfoxylate (SFS) | 3.1 |
| HCl | 17.7 |
| water | qs to 1000 mL |

The propylene glycol, the PVP, and a portion of the water were combined and agitated until the PVP dissolved. After the solution was heated to about 50° C., the magnesium oxide was added. The danofloxacin mesylate was added to the resulting slurry. Agitating for approximately one hour at about 50° C., the formulation was brown with suspended material. The formulation was cooled to room temperature, and the pH was adjusted to 7.9 with the HCl. The formulation was agitated overnight. After additional agitation, it was amber and contained some suspended material. A sufficient quantity of water was added to produce a 1000 mL solution with a pH of 8.0.

The solution contained 180 mg/mL of danofloxacin based on a potency of 759 mg/g for the lot of danofloxacin mesylate used.

EXAMPLE 18

|  | g/1500 mL |
| --- | --- |
| danofloxacin mesylate | 237.2 |
| polyethylene glycol 300 (PEG) | 251.5 |
| polyvinylpyrrolidone (PVP) | 50.1 |
| MgO | 20.2 |
| sodium formaldehyde sulfoxylate (SFS) | 3.1 |
| HCl | 51.9 |
| water | qs to 1500 mL |

The PEG, the PVP, and a portion of the water necessary to produce 1000 mL of a formulation containing 25% PEG and 5% PVP were combined and agitated until the PVP dissolved. The solution was heated to about 50° C., and the magnesium oxide was added. The danofloxacin mesylate was added to the resulting slurry, which was then agitated for approximately one hour at about 50° C. The formulation was light brown and contained a considerable amount of suspended material. After cooling to room temperature, it became a semi-solid with a pH of 7.9. Approximately 500 mL of water was added, the pH was adjusted to 6.2 with HCl, and the formulation was agitated overnight. After additional agitation, a clear amber solution was formed with a pH of 5.5 and containing a few large suspended particles. After the pH was adjusted to 6.1 with the NaOH, the formulation was amber and contained some suspended material. A sufficient quantity of water was added to produce a 1500 mL solution at a pH of 6.2.

The solution contained 120 mg/mL of danofloxacin based on a potency of 759 mg/g for the lot of danofloxacin mesylate used.

EXAMPLE 19

|  | g/4000 mL |
| --- | --- |
| danofloxacin mesylate | 949 |
| 2-pyrrolidone | 800 |
| polyvinylpyrrolidone (PVP) | 200 |
| MgO | 81 |
| HCl | 174 |
| liquefied phenol | 11 |
| sodium formaldehyde sulfoxylate (SFS) | 10 |
| water | qs to 4000 mL |

The 2-pyrrolidone, the PVP, and a portion of the water necessary to produce 4000 mL of the formulation were combined and agitated until the PVP dissolved. Most of the HCl was added to the solution, then the magnesium oxide was added. The danofloxacin mesylate was added to the resulting slurry to form a dark brown solution with suspended material. After the formulation was agitated overnight and the pH adjusted to 7.5 with the remainder of the HCl, the formulation was dark brown with a small amount of suspended material. The liquefied phenol was added, the SFS was added, and a sufficient quantity of water was added to produce 4000 mL of a solution with a pH of 7.5.

The solution contained 180 mg/mL of danofloxacin based on a potency of 759 mg/g for the lot of danofloxacin mesylate used.

EXAMPLE 20

|  | g/206 mL |
| --- | --- |
| danofloxacin mesylate | 59.53 |
| N-methylpyrrolidone | 70.19 |
| propylene glycol | 30.06 |
| MgO | 9.97 |
| HCl | 4.13 |
| water | qs to 206 mL |

A portion of the water, a portion of the N-methylpyrrolidone, and the PVP were combined and agitated until the PVP dissolved. A portion of the HCl was added, and then the magnesium oxide. After addition of the danofloxacin mesylate to the resulting slurry, the formulation was stirred overnight. The clear amber/gold solution having a few suspending particles, was held for an additional 36 hours. The pH of the formulation was 8.0. The remainder of the HCl and the water were added, resulting in a pH of 7.5.

The solution contained 175 mg/mL of danofloxacin based on a potency of 759 mg/g for the lot of danofloxacin mesylate used.

EXAMPLE 21

|  | g/200 mL |
| --- | --- |
| danofloxacin mesylate | 47.49 |
| N-methylpyrrolidone | 20.01 |
| propylene glycol | 30.01 |
| polyvinylpyrrolidone (PVP) | 10.03 |
| MgO | 4.09 |
| HCl | 7.44 |
| water | qs to 200 mL |

A portion of the water, the N-methylpyrrolidone, and the PVP were combined and agitated until the PVP dissolved. A portion of the HCl was added, and then the magnesium oxide. After the danofloxacin mesylate was added to the resulting slurry, the formulation was stirred overnight. A clear gold solution with a few suspended particles was formed and held for an additional 36 hours. After the propylene glycol was added, the pH of the formulation was 7.9. The remainder of the HCl and the water were added, resulting in a pH of 7.6.

The solution contained 180 mg/mL of danofloxacin based on a potency of 759 mg/g for the lot of danofloxacin mesylate used.

We claim:

1. An aqueous pharmaceutical solution which is suitable for injection into a host comprising danofloxacin or a pharmaceutically acceptable salt thereof in an amount of about 120 to about 200 mg/ml, and (1) magnesium oxide or magnesium chloride, or (2) zinc oxide or zinc acetate in admixture with a co-solvent selected from at least one of 2-pyrrolidone, propylene glycol, polyethylene glycol, or N-methyl-pyrrolidone; said magnesium and zinc compound and said co-solvent being present in amounts which are sufficient for improved toleration at the injection site.

2. A solution according to claim 1 wherein said danofloxacin or said salt thereof is present in an amount of about 180 mg/ml.

3. A solution according to claim 1 wherein said magnesium compound is present together with a co-solvent selected from at least one of 2-pyrrolidone, propylene glycol, polyethylene glycol, and N-methyl-pyrrolidone.

4. A solution according to claim 3 wherein said magnesium compound is present together with said co-solvent and polyvinylpyrrolidone.

5. A solution according to claim 1 wherein said solution in addition contains an antioxidant.

6. A solution according to claim 5 wherein said antioxidant is sodium formaldehyde sulfoxylate.

7. A solution according to claim 5 wherein said antioxidant is thioglycerol.

8. A solution according to claim 1 wherein said solution in addition contains components to adjust the pH of said solution to about 5 to about 9.5.

9. A solution according to claim 5 wherein the pH of said solution is from about 6.5 to about 9.0.

10. An aqueous pharmaceutical solution which is suitable for injection into a host comprising 180 mg/ml of danofloxacin or a pharmaceutically acceptable salt thereof, magnesium oxide in about an equimolar amount with danofloxacin or said salt thereof, about 20% by weight of 2-pyrrolidone, about 5% by weight of the solution of polyvinylpyrrolidone, and an antioxidant, said solution having a pH of about 7.5.

11. A solution according to claim 10 wherein said antioxidant is thioglycerol.

12. A method for the treatment of a bacterial infection in a host comprising subcutaneously injecting into said host an aqueous pharmaceutical solution comprising danofloxacin or a pharmaceutically acceptable salt thereof in an amount of about 120 to 200 mg/ml sufficient for the treatment of bacterial infections, and (1) magnesium oxide or magnesium chloride, or (2) zinc oxide or zinc acetate in admixture with a co-solvent selected from at least one of 2-pyrrolidone, propylene glycol, polyethylene glycol, and N-methyl-pyrrolidone; said magnesium or zinc compound and said co-solvent being present in amounts which are sufficient for improved toleration at the injection site.

* * * * *